United States Patent [19]

Schmidt et al.

[11] Patent Number: 5,004,859

[45] Date of Patent: Apr. 2, 1991

[54] CATALYST FOR THE ISOMERIZATION OF ALKANES

[75] Inventors: Robert J. Schmidt; Robert S. Haizmann, both of Rolling Meadows; Mark R. Ford, Buffalo Grove; C. David Low, Lisle; Frank H. Adams, LaGrange Park, all of Ill.

[73] Assignee: UOP, Des Plaines, Ill.

[21] Appl. No.: 435,304

[22] Filed: Nov. 13, 1989

[51] Int. Cl.$^5$ .............................................. C07C 5/22
[52] U.S. Cl. .................................. 585/741; 585/744; 585/748; 585/750
[58] Field of Search ............... 585/734, 741, 744, 747, 585/748, 751, 740, 746

[56] References Cited

U.S. PATENT DOCUMENTS

| | | | |
|---|---|---|---|
| 2,900,425 | 8/1959 | Bloch et al. | 260/666 |
| 2,924,629 | 2/1960 | Donaldson | 260/666 |
| 2,999,074 | 9/1961 | Bloch et al. | 252/442 |
| 3,031,419 | 4/1962 | Hoekstra | 252/442 |
| 3,259,589 | 7/1966 | Michalko | 252/446 |
| 3,285,984 | 11/1966 | Goble | 585/269 |
| 3,367,888 | 2/1968 | Hoekstra | 252/466 |
| 3,388,077 | 6/1968 | Hoekstra | 252/466 |
| 3,651,167 | 3/1972 | Rosset | 260/681.5 |
| 3,720,628 | 3/1973 | Hayes et al. | 585/741 |
| 3,897,368 | 7/1975 | Ohara et al. | 252/459 |
| 3,931,054 | 1/1976 | Lester | 252/466 |
| 3,963,643 | 6/1976 | Germanas et al. | 252/442 |
| 4,431,750 | 2/1984 | McGinnis et al. | 502/329 |
| 4,520,223 | 5/1985 | McGinnis et al. | 208/138 |
| 4,556,646 | 12/1985 | Bezman | 502/66 |
| 4,716,143 | 12/1987 | Imai | 502/328 |
| 4,762,960 | 8/1988 | Imai et al. | 585/660 |
| 4,786,625 | 11/1988 | Imai et al. | 502/326 |
| 4,827,072 | 5/1989 | Imai et al. | 585/443 |
| 4,880,764 | 11/1989 | Imai et al. | 585/660 |

*Primary Examiner*—Anthony McFarlane
*Attorney, Agent, or Firm*—Thomas K. McBride; John F. Spears, Jr.; Richard E. Conser

[57] ABSTRACT

An improved catalyst particle is disclosed for the conversion of hydrocarbons which comprises a refractory inorganic-oxide support, a Friedel-Crafts metal halide, and a surface-layer platinum-group metal component, wherein the concentration of platinum-group metal component on the surface layer of each catalyst particle is at least 1.5 times the concentration in the central core of the catalyst particle. An isomerization process also is disclosed which is particularly effective for the conversion of $C_4$–$C_7$ alkanes.

4 Claims, 2 Drawing Sheets

CATALYST FOR THE ISOMERIZATION OF ALKANES

BACKGROUND OF THE INVENTION

1. Field of the Invention

This invention relates to an improved catalyst useful in the conversion of hydrocarbons, particularly for the isomerization of alkanes.

2. General Background

The isomerization of light naphtha is an increasingly important process for the upgrading of petroleum refiners' gasoline pool. The widespread removal of lead antiknock additive from gasoline and the rising demands of high-performance internal-combustion engines are increasing the need for "octane," or knock resistance, in the gasoline pool. In the early years of lead removal, refiners relied principally upon increasing the octane of products from catalytic reforming and fluid catalytic cracking operations. Refiners have largely capitalized on these relatively low-cost upgrading options, however, and attention has turned in recent years to upgrading the relatively low-octane high-naphtha component.

Catalyst and process technology for the isomerization of light alkanes is well known in the art. The recent expansion of interest, however, has led to significant improvements in this technology. Catalyst and process developments have led to lower operating temperatures, wherein product octane is favored by isomer equilibrium. Substantial reduction in the hydrogen requirement for a stable operation has resulted in a significant cost reduction, principally through elimination of the need for a hydrogen-recycle system. Both of the aforementioned developments have led toward a predominance of liquid in the isomerization reactor feed, in contrast to the vapor-phase operation of the prior art.

Catalysts exhibiting a dual cracking and hydrogenation-dehydrogenation function are applied widely in the petroleum refining and petrochemical industries to the reforming and isomerization of hydrocarbons. Such catalysts generally have the cracking function imparted by an inorganic oxide, zeolite, or halogen, with a platinum-group component usually imparting the hydrogenation-dehydrogenation function. A catalyst useful in isomerization must be formulated to properly balance its cracking and hydrogenation-dehydrogenation functions to achieve the desired conversion over a prolonged period of time, while effectively utilizing the expensive platinum group metal component.

The performance of a catalyst in isomerization service typically is measured by its activity, selectivity, and stability. Activity refers to the ability of a catalyst to isomerize the reactants into the desired product isomers at a specified set of reaction conditions. Selectivity refers to the proportion of converted feed reacted into the desired product. Stability refers to the rate of change of activity and selectivity during the life of the catalyst. The principal cause of low catalyst stability is the formation of coke, a high-molecular-weight, hydrogen-deficient, carbonaceous material on the catalytic surface. Workers in the isomerization art thus must address the problem of developing catalysts having high activity and stability, and which also either suppress the formation of coke or are not severely affected by the presence of coke.

Currently, workers in the art are faced by the problem of developing cost-effective catalysts meeting the above objectives as a concomitant to the low isomerization temperatures and high proportion of liquid reactants described hereinabove.

3. Related Art

Catalysts containing a platinum-group metal component and a Friedel-Crafts metal halide on a refractory inorganic-oxide binder are known in the art. For example, U.S. Pat. No. 2,900,425 (Bloch et al.) teaches an isomerization process characterized by a catalyst comprising alumina, a platinum-group metal, and a Friedel-Crafts metal halide. Preferably, aluminum chloride is sublimed on to the alumina-platinum composite. Bloch et al. do not disclose a surface-layer platinum-group metal; however, the alternative methods of compositing the platinum-group metal and alumina are all effected before formation of the catalyst particle. See also U.S. Pat. Nos. 2,924,629 (Donaldson), teaching an isomerization process; 2,999,074 (Bloch et al.), teaching a catalyst composition of matter; and 3,031,419, teaching a method for manufacturing a catalyst, none of which disclose a surface-layer platinum-group metal component.

U.S. Pat. No. 3,963,643 (Germanas et al.) teaches a method of manufacturing a catalyst useful in the isomerization of paraffins by compositing a platinum-group metal with alumina and reacting the composite with a Friedel-Crafts metal halide and a polyhalo compound. Germanas et al. teaches away from a surface-layer platinum-group metal, noting that: "It is common practice to impregnate the alumina with an aqueous chloroplatinic acid solution acidified with hydrochloric acid to facilitate an even distribution of platinum on the alumina . . ." (col. 2, lines 49–53).

The layering of a platinum-group metal component in a catalyst particle has been disclosed in the prior art. U.S. Pat. Nos. 3,259,589 (Michalko), 3,388,077 (Hoekstra) and 3,931,054 (Lester) teach a catalyst preparation method for providing a subsurface-layer of Group VIII metal or platinum in a catalyst particle. U.S. Pat. No. 3,367,888 (Hoekstra) discloses a method of catalyst preparation wherein the Group VIII metal is deposited on the outer surface of the carrier. U.S. Pat. No. 3,651,167 (deRosset) teaches a hydrogenation process characterized by a catalyst comprising a surface-impregnated Group VIII metal or alumina. U.S. Pat. Nos. 3,897,368 (Ohara) and 4,431,750 (McGinnis) disclose catalyst preparation methods wherein a noble or platinum-group metal is deposited in high concentration on the surface of the support. U.S. Pat. Nos. 4,520,223 teaches a method of preparation of a surface-impregnated noble metal catalyst useful in a dehydrogenation process. U.S. Pat. Nos. 4,716,143 (Imai) and 4,786,625 (Imai et al.) disclose catalysts comprising surface-impregnated platinum, but teach that the catalysts decrease undesirable side reactions such as isomerization. U.S. Pat. No. 4,556,646 (Bezman) teaches a catalyst with an even radial distribution of noble metal, and reveals that low penetration of Pd into a catalyst base increases coking in a hydrocracking reaction. Further, none of these patents disclose the essential Friedel-Crafts metal halide component of the present catalyst.

Thus, no suggestion is offered, in well over 20 years of prior art pertaining to individual components of the present catalyst particle, to combine a Friedel-Crafts metal halide and a surface-layer platinum-group metal component on a refractory inorganic-oxide support. In conformity with the unpredictability of catalytic effects, the surprising benefits of this catalyst particle are observed specifically in the context of modern, primarily liquid-phase, isomerization operations.

SUMMARY OF THE INVENTION

Objects

It is an object of the present invention to provide a novel catalyst particle, useful particularly for the isomerization of isomerizable hydrocarbons. A corollary object of the invention is to provide a process for isomerizing isomerizable hydrocarbons, particularly alkanes having from four to seven carbon atoms per molecule.

Summary

This invention is based on the discovery that a catalyst particle having a Friedel-Crafts metal halide and a surface-layer platinum-group metal on an inorganic-oxide support demonstrates surprising results in increasing the octane number of $C_5/C_6$ naphtha streams.

Embodiments

A broad embodiment of the present invention is a catalyst particle comprising an inorganic-oxide binder, a Friedel-Crafts metal halide, and a surface-layer platinum-group metal component having a surface-layer concentration at least 1.5 times that in the central core of each particle. Alumina is the preferred inorganic-oxide binder, and aluminum chloride is the preferred Friedel-Crafts metal halide. Platinum is the preferred surface-layer platinum-group component.

In a preferred embodiment, an organic polyhalo component is added to the catalyst particle, with carbon tetrachloride being especially preferred.

In another aspect, the invention is a preferred method of preparing the present catalyst by surface-impregnating a platinum-group metal component and vaporizing and subliming the Friedel-Crafts metal component onto the inorganic-oxide binder.

In an alternative embodiment, isomerizable hydrocarbons are isomerized with the present catalyst particle. The preferred feedstock comprises $C_4$-$C_7$ alkanes. These as well as other objects and embodiments will become apparent from the detailed description of the invention.

DESCRIPTION OF THE PREFERRED EMBODIMENTS

To reiterate briefly, one embodiment of the present invention is a catalyst particle comprising an inorganic-oxide binder, a Friedel-Crafts metal halide, and a surface-layer platinum-group metal component having a surface-layer concentration at least 1.5 times that in the central core of each catalyst particle.

Catalyst Support

Considering first the refractory inorganic-oxide support utilized in the present invention, it is preferred that the material be a porous, adsorptive, high-surface-area support having a surface area of about 25 to about 500 $m^2/g$. The porous carrier material should also be uniform in composition and relatively refractory to the conditions utilized in the hydrocarbon conversion process. By the term "uniform in composition," it is meant that the support be unlayered, has no concentration gradients of the species inherent to its composition, and is completely homogeneous in composition. Thus, if the support is a mixture of two or more refractory materials, the relative amounts of these materials will be constant and uniform throughout the entire support. It is intended to include within the scope of the present invention carrier materials which have traditionally been utilized in dual-function hydrocarbon conversion catalysts such as: (1) refractory inorganic-oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (2) ceramics, porcelain, bauxite; (3) silica or silica gel, silicon carbide, clays and silicates including those synthetically prepared and naturally occurring, which may or may not be acid treated, for example attapulgus clay, diatomaceous earth, fuller's earth, kaolin, kieselguhr, etc.; (4) crystalline zeolitic aluminosilicates, such as X-zeolite, Y-zeolite, mordenite, or L-zeolite, either in the hydrogen form or in nonacidic form with one or more alkali metals occupying the cationic exchangeable sites; (5) nonzeolitic molecular sieves, such as aluminophosphates or silico-aluminophosphates; (6) spinels such as $MgAl_2O_4$, $FeAl_2O_4$, $ZnAl_2O_4$, $CaAl_2O_4$, and other like compounds having the formula $MO$-$Al_2O_3$ where M is a metal having a valence of 2; and (7) combinations of materials from one or more of these groups.

The preferred refractory inorganic-oxide for use in the present invention is alumina. Suitable alumina materials are the crystalline aluminas known as the gamma-, eta-, and theta-alumina, with gamma- or eta-alumina giving best results. The preferred refractory inorganic-oxide will have an apparent bulk density of about 0.3 to about 1.01 g/cc and surface area characteristics such that the average pore diameter is about 20 to 300 angstroms, the pore volume is about 0.1 to about 1 cc/g, and the surface area is about 100 to about 500 $m^2/g$.

A particularly preferred alumina is that which has been characterized in U.S. Pat. Nos. 3,852,190 and 4,012,313 as a by-product from a Ziegler higher alcohol synthesis reaction as described in Ziegler's U.S. Pat. No. 2,892,858. For purposes of simplification, such an alumina will be hereinafter referred to as a "Ziegler alumina." Ziegler alumina is presently available from the Vista Chemical Company under the trademark "Catapal" or from Condea Chemie GMBH under the trademark "Pural." This material is an extremely high purity pseudoboehmite powder which, after calcination at a high temperature, has been shown to yield a high-purity gamma-alumina.

The alumina powder may be formed into a suitable catalyst material according to any of the techniques known to those skilled in the catalyst-carrier-forming art. Spherical carrier particles may be formed, for example, from this Ziegler alumina by: (1) converting the alumina powder into an alumina sol by reaction with a suitable peptizing acid and water and thereafter dropping a mixture of the resulting sol and a gelling agent into an oil bath to form spherical particles of an alumina gel which are easily converted to a gamma-alumina carrier material by known methods; (2) forming an extrudate from the powder by established methods and thereafter rolling the extrudate particles on a spinning disk until spherical particles are formed which can then be dried and calcined to form the desired particles of spherical carrier material; and (3) wetting the powder with a suitable peptizing agent and thereafter rolling the particles of the powder into spherical masses of the desired size. This alumina powder can also be formed in any other desired shape or type of carrier material known to those skilled in the art such as rods, pills, pellets, tablets, granules, extrudates, and like forms by methods well known to the practitioners of the catalyst material forming art.

The preferred type of carrier material for the present invention is a cylindrical extrudate generally having a diameter of about 0.75 to 3.3 mm, with about 1.6 mm being especially preferred. The length-to-diameter ratio is about 1:1 to 5:1, with about 2:1 being especially preferred. The preferred extrudate particle form of the carrier material is preferably prepared by mixing the alumina powder with water and suitable peptizing agents such as nitric acid, acetic acid, aluminum nitrate, and the like material until an extrudable dough is formed. The amount of water added to form the dough is typically sufficient to give a Loss on Ignition (LOI) at 500° C. of about 45 to 65 mass %, with a value of 55 mass % being especially preferred. On the other hand, the acid addition rate is generally sufficient to provide 2 to 7 mass % of the volatile-free alumina powder used in the mix, with a value of 3 to 4 mass % being especially preferred. The resulting dough is then extruded through a suitably sized die to form extrudate particles.

The extrudate particles are dried at a temperature of about 150° to about 200° C., and then calcined at a temperature of about 450° to 800° C. for a period of 0.5 to 10 hours to effect the preferred form of the refractory inorganic-oxide. It is preferred that the refractory inorganic-oxide comprise substantially pure gamma alumina having an apparent bulk density of about 0.6 to about 1 g/cc and a surface area of about 150 to 280 $m^2/g$ (preferably 185 to 235 $m^2/g$, at a pure volume of 0.3 to 0.8 cc/g).

Platinum-Group Metals

An essential ingredient of the catalyst is the surface-layer platinum-group metal component. Of the platinum group, i.e., platinum, palladium, rhodium, ruthenium, osmium and iridium, palladium is a preferred component and platinum is especially preferred. Mixtures of platinum-group metals also are within the scope of this invention. This component may exist within the final catalytic composite as a compound such as an oxide, sulfide, halide, or oxyhalide, in chemical combination with one or more of the other ingredients of the composite, or as an elemental metal. Best results are obtained when substantially all of this component is present in the elemental state. This component may be present in the final catalyst composite in any amount which is catalytically effective, but relatively small amounts are preferred. In fact, the surface-layer platinum-group metal component generally will comprise about 0.01 to 2 mass % of the final catalyst, calculated on an elemental basis. Excellent results are obtained when the catalyst contains about 0.05 to 1 mass % of platinum.

An essential feature of the catalyst of the present invention is that the platinum-group metal component is concentrated in the surface layer of each catalyst particle. In defining the present invention, a "surface-layer" component has a concentration in the micron surface layer of the catalyst particle that is at least 1.5 times the concentration in the central core of the catalyst particle. Preferably, the surface-layer concentration of platinum-group metal is at least about twice the concentration in the central core. As exemplified hereinbelow, the surface layer may be 100 or 150 microns deep and the central core may be 50% of the volume or 50% of the diameter of the particle; however, other quantitative criteria are not excluded thereby.

"Layer" is a stratum of the catalyst particle of substantially uniform thickness. The "surface layer" is the layer of the catalyst particle adjacent to the surface of the particle. "Diameter" is defined as the minimum regular dimension through the center of the catalyst particle; for example, this dimension would be the diameter of the cylinder of an extrudate. In the examples presented hereinbelow, platinum concentration is measured from the surface to the center, or over the radius, of the catalyst particle. "Central core" is defined in the present invention as a concentric cylindrical portion of a catalyst particle having a volume or diameter that is 50% of the volume or diameter; respectively, of the catalyst particle. As exemplified for the preferred extrudates of the present invention, the central core is a concentric cylindrical portion excluding the surface layer at the ends of the extrudate particles.

The characterization of the platinum-group metal component as a "surface-layer" component is intended to encompass a platinum-group metal component gradient upon and within the catalyst support. The concentration of platinum-group metal component tapers off in progressing from the surface to the center of the catalyst particle. The actual gradient of the platinum-group metal component within the catalyst particle varies depending upon the manufacturing method used to fabricate the catalyst. However, a substantially greater portion of the platinum-group metal component is located outside than within the central core of the catalyst particle. As previously stated, the concentration of the platinum-group metal component in the surface layer of the catalyst is at least 1.5 times and preferably twice the concentration in the central core of the catalyst particle. The gradient of the platinum-group metal component is determined by Scanning Electron Microscopy.

The SEM data show the approximate metals content of any one point within the catalyst pill, based on the metals distribution profile in relation to the alumina level. The result of each analysis may not be basd upon a zero point; attempting to integrate a distribution curve is not possible, and could lead to interpretation errors as the entire curve could be shifted either up or down. However, the data are useful for making relative comparisons of metal distributions.

Although the reasons for the surprising improvement in performance are not well understood, the application of the present catalyst to a principally liquid-phase operation is believed to be a factor. Operating temperatures required for isomerization of $C_4$-$C_7$ alkanes are lower than in the past, due to improved catalysts such as the present invention. The proportion of hydrogen in the feed stream is significantly lower in modern isomerization units, as discussed hereinafter. Both lower temperatures and lower gas rates result in an increasing proportion of liquid reactants. The length of diffusion paths within the catalyst is believed to be more important for liquid reactants, and the surface-layer metal component thus permits greater facility of access to catalytic sites. This theory is supported by evidence that vapor-phase isomerization operations associated with the prior art do not show the same benefits from a surface-layer platinum-group metal component.

The platinum-group metal component may be incorporated into the catalyst of the present invention by any means suitable to result in a surface-layer component having a concentration in the surface layer of each catalyst particle at least 1.5 times that of the central core of the particle. Best results are obtained when the platinum-group metal component is surface-impregnated. A preferred method of surface impregnating the platinium-group component is by means of a low-acid impregnation utilizing a solution of a soluble, decomposable complex compound of the platinum group component. In general the solvent used in this impregnation step is selected on the basis of its capability to dissolve the desired decomposable complex compound and is a low-acid, preferably aqueous solution. By low-acid it is meant that the impregnation solution generally has a normality of 2 or less. An HCl solution is preferred, but nitric acid and the like also can be used.

Typical platinum-group compounds which may be employed in preparing the catalyst of the invention are chloroplatinic acid, ammonium chloroplatinate, bromoplatinic acid, platinum dichloride, platinum tetrachloride hydrate, platinum dichlorocarbonyl dichloride, dinitrodiaminoplatinum, palladium chloride, palladium chloride dihydrate, palladium nitrate, etc. Chloroplatinic acid is preferred as a source of the especially preferred platinum component. A surface-layer platinum component may be impregnated onto the catalyst from a solution of chloroplatinic acid in the absence of strong mineral acids such as hydrochloric and nitric acid.

The platinum group component may be surface impregnated via the formulation of a chemical complex of the platinum-group metal component which is strongly attracted to the refractory oxide support, resulting in the platinum group metal being retained primarily upon the outer surface of the catalyst. Any compound that is known to complex with the desired platinum-group component and with the metal component of the refractory inorganic-oxide support may be used in the preparation of the catalyst of the present invention. It has been found that a multi-dentated ligand is very useful in complexing with a platinum group metal and the refractory inorganic oxide support., resulting in the surface-impregnation of the platinum-group metal component. Multi-dentated ligands are compounds that contain more than one appendage that can bond strongly to the oxide support. Such appendages would typically comprise carboxylic acids, amino groups, thiol groups, phosphorus groups, or other strongly polar groups of chemical components.

It is also an aspect of this invention that the multi-dentated ligand contains a functional group such as -SH or PR$_2$ (where R is hydrocarbon) that has a high affinity towards the platinum group metal component and a second functional group comprising a carboxylic acid or the like component that can be strongly adsorbed onto the metal oxide support. This preferred property of the multi-dentated ligand effectively insures that the platinum group metal component does not penetrate the catalyst particle, by binding strongly with the platinum group metal while also binding to the support quickly and strongly. Examples of some useful multi-dentated ligands include thiomalic acid, thiolactic acid, mercaptopropionic acid, thiodiacetic acid, thioglycollic acid, and thioproponic acid among others.

It is within the scope of the present invention that the catalyst may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art.

The composite, before addition to the Friedel-Crafts metal halide, is dried and calcined. The drying is carried out at a temperature of about 100° to 300°, followed by calcination or oxidation at a temperature of from about 375° to 600° C. in an air oxygen atmosphere for a period of about 0.5 to 10 hours in order to convert the metallic components substantially to the oxide form.

Halogen Components

Another essential component of the catalyst of the present invention is a Friedel-Crafts metal halide. Suitable metal halides of the Friedel-Crafts type include aluminum chloride, aluminum bromide, ferric chloride, ferric bromide, zinc chloride and the like compounds, with the aluminum halides and particularly aluminum chloride ordinarily yielding best results. Generally, this component can be incorporated into the catalyst of the present invention by way of the conventional methods for adding metallic halides of this type; however, best results are ordinarily obtained when the metallic halide is sublimed onto the surface of the support according to the preferred method disclosed in U.S. Pat. No. 2,999,074, which is incorporated by reference.

In the preferred method, wherein the calcined refractory inorganic-oxide support is impregnated with a Friedel-Crafts metal halide component, the presence of chemically combined hydroxyl groups in the refractory inorganic oxide allows a reaction to occur between the Friedel-Crafts metal halide and the hydroxyl group of the support. For example, aluminum chloride reacts with the hydroxyl groups in the preferred alumina support to yield Al—O—AlCl$_2$ active centers which enhance the catalytic behavior of the catalyst. Since chloride ions and hydroxy ions occupy similar sites on the support, more hydroxyl sites will be available for possible interaction with the Friedel-Crafts metal halide when the chloride population of the sites is low. Therefore, potentially more active Friedel-Crafts type versions of the catalyst will be obtained when the chloride content of the support is the low range of the 0.1 to 10 weight percent range.

The Friedel-Crafts metal halide may be impregnated onto the catalyst by sublimation of the Friedel-Crafts metal halide onto the calcined support under conditions to combine the sublimed Friedel-Crafts metal halide with the hydroxyl groups of the calcined support. This reaction is typically accompanied by the elimination of about 0.5 to about 2.0 moles of hydrogen chloride per mole of Friedel-Crafts metal halide reacted with the inorganic-oxide support. In subliming aluminum chloride, which sublimes at about 184° C., suitable impregnation temperatures range from about 190° C. to 700° C., with a preferable range being from about 200° C. to 600° C. The sublimation can be conducted at atmospheric pressure or under increased pressure and in the presence of absence of diluent gases such a hydrogen or light paraffinic hydrocarbons or both. The impregnation of the Friedel-Crafts metal halide may be conducted batch-wise, but a preferred method for impregnating the calcined support is to pass sublimed AlCl₃ vapors, in admixture with a carrier gas such as hydrogen, through a calcined catalyst bed. This method both continuously deposits and reacts the aluminum chloride and also removes the evolved HCl.

The amount of Friedel-Crafts metal halide combined with the calcined may range from about 1 up to 15 mass % to the Friedel-Crafts metal-halide-free, calcined composite. The final composite containing the sublimed Friedel-Crafts metal halide is treated to remove the unreacted Friedel-Crafts metal halide by subjecting the composite to a temperature above the sublimation temperature of the Friedel-Crafts metal halide for a time sufficient to remove from the composite any unreacted Friedel-Crafts metal halide. In the case of AlCl₃, temperatures of about 400° C. to 600° C. and times of from about 1 to 48 hours are sufficient.

In a preferred embodiment of the present invention, the resultant oxidized catalytic composite is subjected to a substantially water-free and hydrocarbon-free reduction step prior to its use in the conversion of hydrocarbons. This step is designed to selectively reduce the platinum-group component to the corresponding metal and to insure a finely divided dispersion of the metal component throughout the carrier material. Preferably substantially pure and dry hydrogen (i.e., less than 20 vol. ppm H₂O) is used as the reducing agent in this step. The reducing agent is contacted with the oxidized composite at conditions including a temperature of about 425° C. to about 650° C. and a period of time of about 0.5 to 2 hours to reduce substantially all of the platinum-group component to its elemental metallic state. This reduction treatment may be performed in situ as part of a start-up sequence if precautions are taken to predry the plant to a substantially water-free state and if substantially water-free and hydrocarbon-free hydrogen is used.

An optional component of the present catalyst is an organic polyhalo component. In this embodiment, the Friedel-Crafts metal-halide-containing composite is further treated in contact with a polyhalo compound containing at least 2 chlorine atoms and selected from the group consisting of methylene halide, haloform, methylhaloform, carbon tetrahalide, sulfur dihalide, sulfur halide, thionyl halide, and thiocarbonyl tetrahalide. Suitable polyhalo compounds thus include methylene chloride, chloroform, methylchloroform, carbon tetrachloride, and the like. In any case, the polyhalo compound must contain at least two chlorine atoms attached to the same carbon atom. Carbon tetrachloride is the preferred polyhalo compound.

The composite contacts the polyhalo compound preferably diluted in a non-reducing gas such as nitrogen, air, oxygen and the like. The contacting suitably is effected at a temperature of from about 100° to 600° C. over a period of from about 0.2 to 5 hours to add at least 0.1 mass % combined halogen to the composite. The improvement in performance of the catalyst is not as substantial when the inorganic-oxide support is first treated with a polyhalo compound before compositing with the Friedel-Crafts metal halide.

The catalyst of the present invention may contain an additional halogen component. The halogen component may be either fluorine, chlorine, bromine or iodine or mixtures thereof. Chlorine is the preferred halogen component. The halogen component is generally present in a combined state with the inorganic-oxide support. Although not essential to the invention, the halogen component is preferably well dispersed throughout the catalyst. The halogen component may comprise from more than 0.2 to about 15 wt. %, calculated on an elemental basis, of the final catalyst.

The halogen component may be incorporated in the catalyst in any suitable manner, either during the preparation of the inorganic-oxide support or before, while or after other catalytic components are incorporated. For example, the alumina sol utilized to form the preferred alumina carrier material may contain halogen and thus contribute at least some portion of the halogen content in the final catalyst. The halogen component or a portion thereof also may be added to the catalyst during the incorporation of other catalyst components into the support, for example, by using chloroplatinic acid in impregnating a platinum component. Also, the halogen component or a portion thereof may be added to the catalyst by contacting with the halogen or a compound, solution, suspension or dispersion containing the halogen before or after other catalyst components are incorporated into the support. Suitable compounds containing the halogen include acids containing the halogen, for example, hydrochloric acid. Alternatively, the halogen component or a portion thereof may be incorporated by contacting the catalyst with a compound, solution, suspension or dispersion containing the halogen in a subsequent catalyst regeneration step.

Process

In the process of the present invention, an isomerizable hydrocarbon charge stock, preferably in admixture with hydrogen, is contacted with a bed of catalyst particles of the type hereinbefore described in a hydrocarbon isomerization zone. Contacting may be effected using the catalyst in a fixed-bed system, a moving-bed system, a fluidized-bed system, or in a batch-type operation. In view of the danger of attrition loss of the valuable catalyst and of operational advantages, it is preferred to use a fixed-bed system. In this system, a hydrogen-rich gas and the charge stock are preheated by suitable heating means to the desired reaction temperature and then passed into an isomerization zone containing a fixed bed of the catalyst particle as previously characterized. The isomerization zone may be in a single reactor or in two or more separate reactors with suitable means therebetween to insure that the desired isomerization temperature is maintained at the entrance to each zone. Two or more reactors in sequence are preferred to enable improved isomerization through control of individual reactor temperatures and for partial catalyst replacement without a process shutdown. The reactants may be contacted with the bed of catalyst particles in either upward, downward, or radial flow fashion. The reactants may be in the liquid phase, a mixed liquid-vapor phase, or a vapor phase when contacted with the catalyst particles, with excellent results being obtained by application of the present invention to a primarily liquid-phase operation.

Feedstocks

In the group of isomerizable hydrocarbons suitable as feedstock to the process of the present invention, alkanes having from 4 to 7 carbon atoms per molecule ($C_4$–$C_7$) are preferred. These may be contained in such streams from petroleum refining or synthetic-fuel production as light straight-run naphtha, light natural gasoline, light reformate, light raffinate from aromatics extraction, light cracked naptha, normal-butane concentrate, field butanes and the like. An especially preferred feedstock is light straight-run naphtha, containing more than 50% of $C_5$ and $C_6$ paraffins with a high concentration of low-octane normal paraffins; this feedstock is particularly susceptible to octane-number upgrading by isomerization. The light straight-run naphtha and other feedstocks also may contain naphthenes, aromatics, olefins, and hydrocarbons heavier than $C_6$. The olefin content should be limited to a maximum of 10% and the content of hydrocarbons heavier than $C_6$ to 20% for effective control of hydrogen consumption, cracking reactions, heat of reaction and catalyst activity.

It is generally known that high-chloride platinum-alumina catalysts of this type are highly sensitive to sulfur- and oxygen-containing compounds. The feedstock therefore must be relatively free of such compounds, with a sulfur concentration generally no greater than 0.5 ppm. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high-activity chloride from the catalyst and replacing it with inactive aluminum hydroxide. Therefore, water and oxygenates that can decompose to form water can only be tolerated in very low concentrations. In general, this requires a limitation of oxygenates in the feed to about 0.1 ppm or less. The feedstock may be treated by any method that will remove water and sulfur compounds. Sulfur may be removed from the feed stream by hydrotreating. Adsorption systems for the removal of sulfur and water from hydrocarbon streams are well known to those skilled in the art.

Operating Conditions

Hydrogen is admixed with the isomerizable hydrocarbon feed to provide a mole ratio of hydrogen to hydrocarbon feed of about 0.01 to 5. The hydrogen may be supplied totally from outside the process or supplemented by hydrogen recycled to the feed after separation from reactor effluent. Light hydrocarbons and small amounts of inerts such as nitrogen and argon may be present in the hydrogen. Water should be removed from hydrogen supplied from outside the process, preferably by an adsorption system as is known in the art.

Although there is no net consumption of hydrogen in the isomerization reaction, hydrogen generally will be consumed in a number of side reactions such as cracking, disproportionation, and aromatics and olefin saturation. Such hydrogen consumption typically will be in a mol ratio to the hydrocarbon feed of about 0.03 to 0.1. Hydrogen in excess of consumption requirements is maintained in the reaction zone to enhance catalyst stability and maintain conversion by compensation for variations in feed composition, as well as to suppress the formation of carbonaceous compounds, usually referred to as coke, which foul the catalyst particles.

In a preferred embodiment, the hydrogen to hydrocarbon mol ratio in the reactor effluent is equal to or less than 0.05. Generally, a mol ratio of 0.05 or less obviates the need to recycle hydrogen from the reactor effluent to the feed. It has been found that the amount of hydrogen needed for suppressing coke formation need not exceed dissolved hydrogen levels. The amount of hydrogen in solution at the normal conditions of the reactor effluent will usually be in a ratio of from about 0.02 to less 0.01. The amount of excess hydrogen over consumption requirements that is required for good stability and conversion is in a ratio of hydrogen to hydrocarbons of from 0.01 to less than 0.05 as measured at the effluent of the isomerization zone. Adding the dissolved and excess hydrogen proportions show that the 0.05 hydrogen to hydrocarbon ratio at the effluent will satisfy these requirements for most feeds. The catalyst particles of the present invention show excellent results in a primarily liquid-phase process operation with reactor-effluent hydrogen-to-hydrocarbon mol ratios of 0.05 or less.

Reactor temperatures will usually range from about 40° to 250° C. Lower reaction temperatures are generally preferred since the equilibrium favors higher concentrations of isoalkanes relative to normal alkanes. Lower temperatures are particularly useful in processing feeds composed of $C_5$ and $C_6$ alkanes, as lower temperatures favor equilibrium mixtures having the highest concentration of high-octane highly branched isoalkanes. When the feed mixture is primarily $C_5$ and $C_6$ alkanes, temperatures in the range of from about 40° to about 150° C. are preferred. When it is desired to isomerize significant amounts of butanes, higher reaction temperatures in the range from about 145° to 225° C. are required to maintain catalyst activity.

Reactor operating pressures generally range from about atmospheric to 100 atmospheres, with preferred pressures in the range of from 20 to 35 atmospheres. Liquid hourly space velocities range from about 0.25 to about 12 volumes of isomerizable hydrocarbon feed per hour per volume of catalyst, with a range of about 0.5 to 5 $hr^{-1}$ being preferred.

The isomerization process also requires the presence of a small amount of an organic chloride promoter. The organic chloride promoter serves to maintain a high level of active chloride on the catalyst particles, as low levels are continuously stripped off the catalyst by the hydrocarbon feed. The concentration of promoter in the combined feed is maintained at from 30 to 300 mass ppm. The preferred promoter compound is carbon tetrachloride. Other suitable promoter compounds include oxygen-free decomposable organic chlorides such as propyldichloride, butylchloride, and chloroform, to name only a few of such compounds. The need to keep the reactants dry is reinforced by the presence of the organic chloride compound which may convert, in part, to hydrogen chloride. As long as the hydrocarbon feed and hydrogen are dried as described hereinabove, there will be no adverse effect from the presence of small amounts of hydrogen chloride.

Recycle Operation

The isomerization product from the especially preferred light-naphtha feedstock will contain some low-octane normal paraffins and intermediate-octane methylhexanes as well as the desired highest-octane isopentane and dimethylbutane. It is within the scope of the present invention that the liquid product from the process is subjected to separate and recycle the lower-octane portion of this product to the isomerization reaction. Generally, low-ocatane normal paraffins may be separated and recycled to upgrade the octane number of the net product. Less-branched $C_6$ and $C_7$ paraffins also may be separated and recycled, along with lesser amounts of hydrocarbons which are difficult to separate from the recycle. Techniques to achieve this separation are well known in the art, and include fractionation and molecular sieve adsorption.

The catalyst and process of the present invention reduce the attractiveness of the aforementioned recycle provisions by achieving higher conversion to desired products without recycle than are realized by applying the prior art.

The following examples are presented to elucidate the catalyst and process of the present invention. These examples are offered as illustrative embodiments and should not be interpreted as limiting the claims.

EXAMPLE I

A control catalyst of the prior art was prepared in order to demonstrate the advantages of the present catalyst.

An extruded alumina base of the prior art, having a particle diameter of about 1600 microns, was vacuum-impregnated in a solution of 3.5 mass % chloroplatinic acid, 2 mass % hydrochloric acid, and 3.5% mass % nitric acid in a volume ratio of 9 parts solution to 10 parts base to obtain a peptized base material having a platinum to base ratio of approximately 0.9. The resulting mixture was cold-rolled for approximately 1 hour and evaporated until dry. The composite then was oxidized and the chloride content adjusted by contact with an IM hydrochloric acid solution at 525° C. at a rate of 45 cc/hour for 2 hours. The composite was then reduced in electrolytic hydrogen at 565° C. for approximately 2 hours and was found to contain approximately 0.25 wt. % Pt and approximately 1 wt. % chloride. Impregnation of active chloride to a level of approximately 5.5 wt. % was accomplished by sublimating aluminum chloride with hydrogen and contacting the catalyst with the sublimated aluminum chloride for approximately 45 minutes at 550° C.

This catalyst was designated "Catalyst A" and contained approximately 0.247 mass % platinum and 5.5 mass % chloride.

EXAMPLE II

"Catalyst B" was prepared in accordance with the invention, with approximately the same platinum level as Catalyst A in order to determine the effect of surface-layer platinum. Catalyst B was prepared from the same extruded alumina base of the prior art used for Catalyst A of Example I.

Example B was prepared by evaporative impregnation of the extruded base with a solution of 3.5 mass % chloroplatinic acid, not containing any effective concentration of hydrochloric or nitric acid in order to prevent uniform platinum penetration into the support, in a volume ratio of 9 parts acid to 10 parts base. The resulting mixture was cold-rolled for approximately 1 hour and evaporated until dry. The composite then was oxidized and the chloride content adjusted by contact with a 1M hydrochloric acid solution at 525° C. at a rate of 45 cc/hr for 2 hours. The composite then was reduced in electrolytic hydrogen at 565° C. for approximately 2 hours and was found to contain approximately 0.25 wt. % Pt and 1 wt. % chloride. Impregnation of active chloride to a level of approximately 5.5 wt. % was accomplished by sublimating aluminum chloride with hydrogen and contacting the catalyst with the sublimated aluminum chloride for approximately 45 minutes at 550° C.

Catalyst B contained approximately 0.242 mass % platinum and 5.8 mass % chloride.

EXAMPLE III

"Catalyst C" was prepared in accordance with the invention, with approximately half the platinum level of Catalyst A in order to determine the effect of surface-layer platinum on platinum requirements for the catalyst. Catalyst C was prepared from the same extruded alumina base of the prior art used for Catalyst A of Example I.

Catalyst C was prepared by vacuum impregnation of the extruded base with a solution of 3.5 mass % chloroplatinic acid, not containing any effective concentration of hydrochloric or nitric acid, in a volume ratio of 9 parts acid to 10 parts base. The resulting mixture was cold-rolled for approximately 1 hour and evaporated until dry. The composite then was oxidized and the chloride content adjusted by contact with a 1M hydrochloric acid solution at 525° C. at a rate of 45 cc/hour for 2 hours. The composite then was reduced in electrolytic hydrogen at 565° C. for approximately 2 hours and was found to contain approximately 0.125 wt. % Pt and 1 wt. % chloride. Impregnation of active chloride to a level of approximately 5.5 wt. % was accomplished by sublimating aluminum chloride with hydrogen on contacting the catalyst with the sublimated aluminum chloride for approximately 45 minutes at 550° C.

Catalyst C contained approximately 0.129 mass % platinum and 5.5 mass % chloride.

EXAMPLE IV

Catalyst particles A, B and C were evaluated by Scanning Election Microscopy (SEM). The purpose of this analysis was to identify the distribution of platinum across the radius of catalyst particles A, B and C. Six particles each of A and B and three of C were evaluated in order to provide reliable average data.

The SEM data shows the approximate metals content of any one point within the catalyst pill, as indicated hereinabove, based on the metals distribution profile in relation to the alumina level. However, the data are useful for making relative comparisons of metal distributions.

Figure 1:
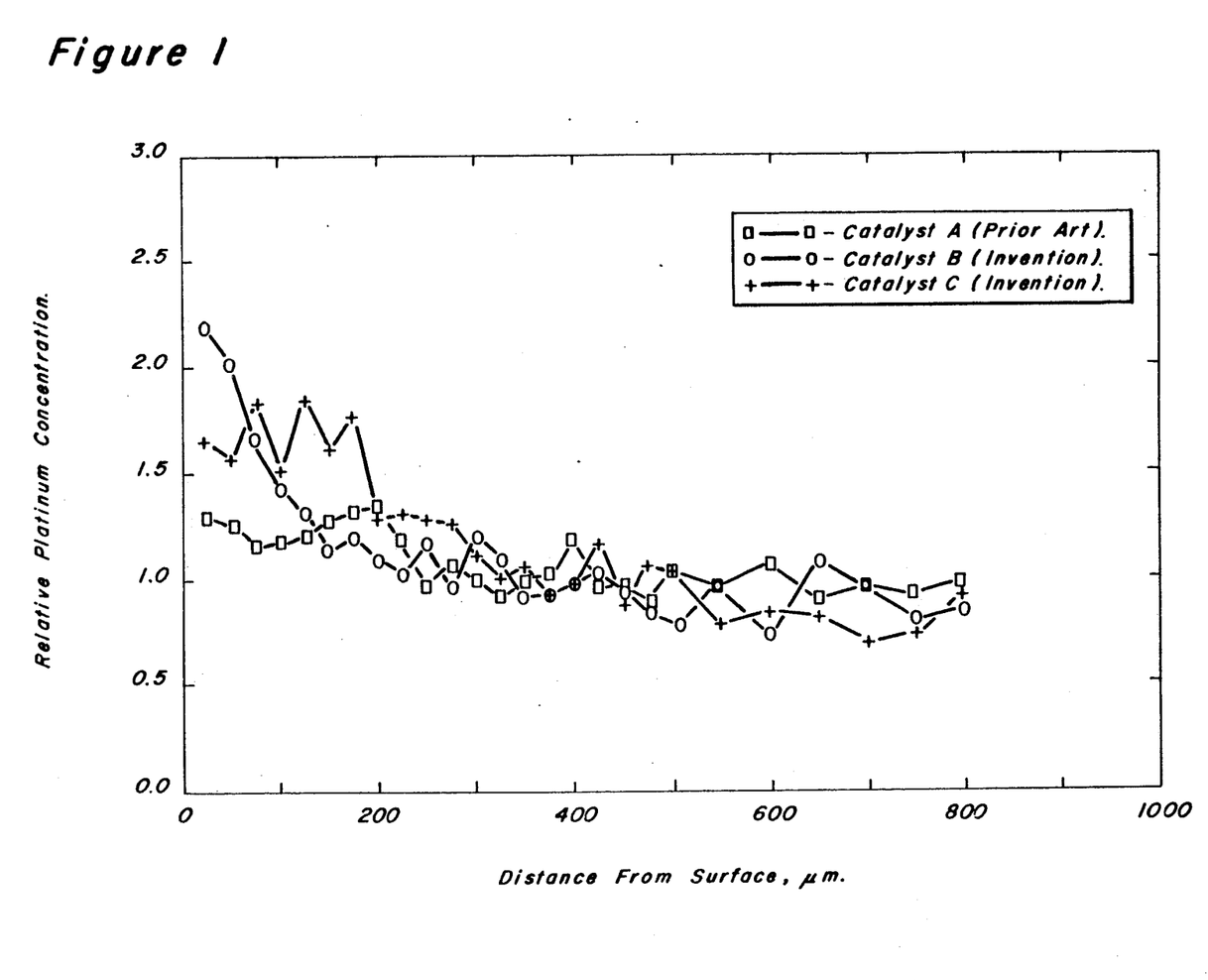
FIG. 1 shows the platinum gradient across the radius of catalyst particles for the Examples described hereinafter. The platinum gradient of a control catalyst particle of the prior art is contrasted with the gradient of catalysts particles of the invention.

FIG. 1 shows the relative distribution of platinum level across the 800-micron radius of the catalyst particles from the surface to the center, relative to the average concentration in the central core representing 50% of the volume of each particle. Catalyst A displayed a relatively even distribution of platinum, with the variation within a region of the catalyst comparable to the difference between the surface layer and central core. Catalysts B and C clearly displayed a relatively high concentration of platinum in the surface layer, with up to about 2.5 times the platinum concentration near the surface relative to the concentration near the center of the catalyst particle.

To quantify the differences between the catalysts of the invention and of the prior art, the platinum concentrations in 100-micron and 150-micron surface layers relative to concentrations in the central core were calculated from the data presented in FIG. 1. Alternative central cores of 50% of the volume of the catalyst particle (considering the ends of the extrudate to be "surface layer") and of 50% of the diameter of the particle were considered. Ratios of concentrations in the surface layer and the central core were as follows:

|  | Catalyst A | Catalyst B | Catalyst C |
|---|---|---|---|
| 100-micron surface layer: | | | |
| 50% - volume central core | 1.26 | 1.88 | 1.67 |
| 50% - diameter central core | 1.31 | 2.02 | 1.87 |
| 150-micron surface layer: | | | |
| 50% - volume central core | 1.27 | 1.55 | 1.70 |
| 50% - diameter central core | 1.32 | 1.66 | 1.91 |

EXAMPLE V

Catalysts A, B and C were tested for relative performance in isomerization service. The same feedstock was used for each of the catalyst tests, and was a hydrotreated light straight-run naphtha having the following composition in mass %.

| $C_3$ | 0.1 |
|---|---|
| n-Butane | 0.3 |
| i-Butane | 0.5 |
| n-Pentane | 28.3 |
| i-Pentane | 18.0 |
| Cyclopentane | 3.6 |
| n-Hexane | 10.7 |
| 2-Methylpentane | 13.5 |
| 3-Methylpentane | 7.5 |
| 2,3-Dimethylbutane | 2.2 |
| 2,2-Dimethylbutane | 2.3 |
| Methylcyclopentane | 4.7 |
| Cyclohexane | 1.8 |
| Benzene | 2.3 |
| $C_7^+$ | 4.2 |
| Total | 100.0 |

Once-through isomerization tests were performed at 450 psig, 1.0 liquid hourly space velocity, and 0.3 hydrogen to hydrocarbon mol ratio and a series of temperatures.

Figure 2:
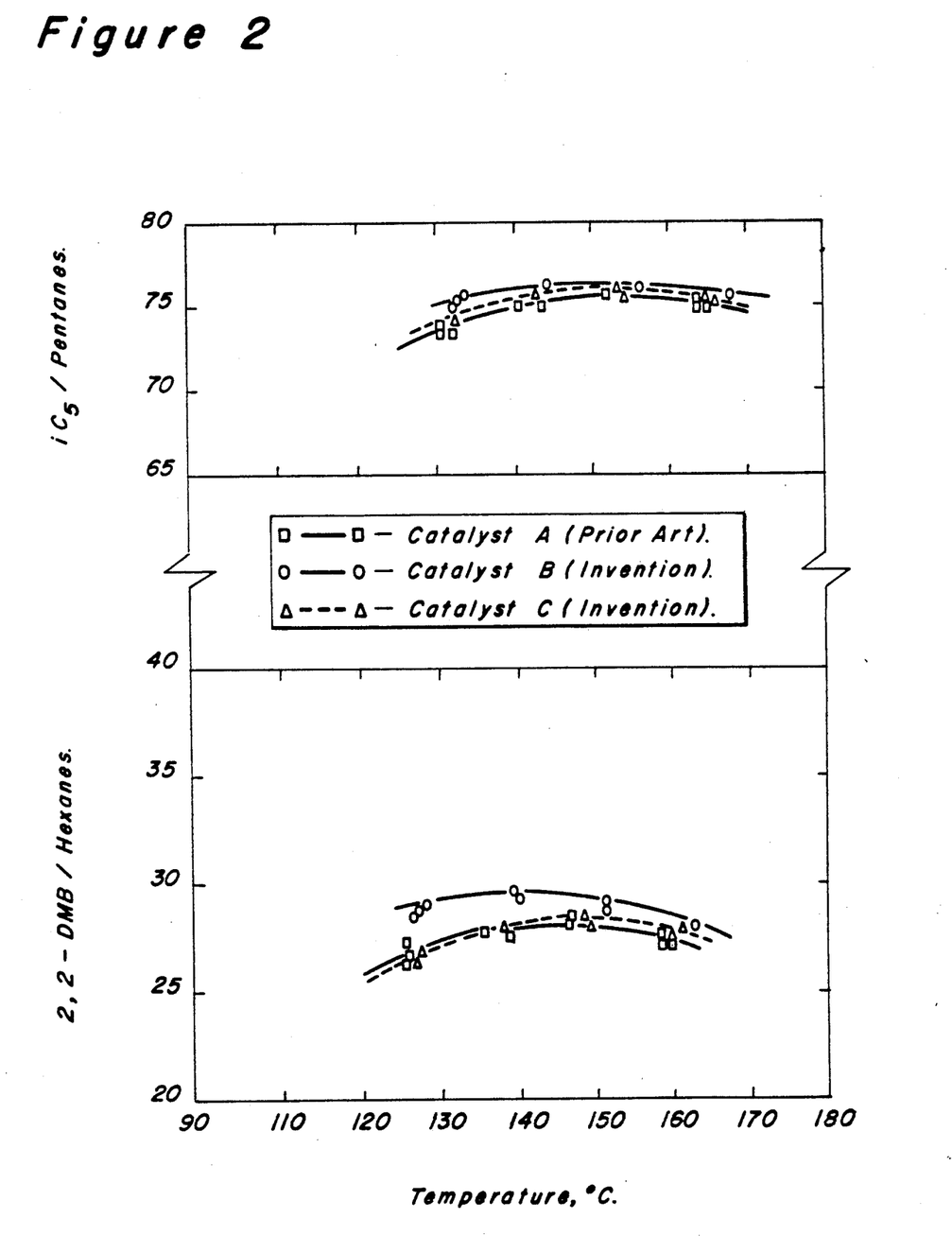
FIG. 2 shows comparative product isomer distribution from the isomerization of a light naphtha stream using catalyst particles containing surface-layer platinum contrasted with results using catalyst particles containing uniformly distributed platinum. Alternative levels of platinum on catalyst also are shown in order to show the impact on platinum requirements of concentrating the platinum in the surface-layer.

The results are shown in FIG. 2 as curves of the product mass ratios of isopentane to total pentanes and 2,2-dimethylbutane ("2,2-DMB") to total hexanes. These ratios are more sensitive tests of catalyst performance than octane-number measurements, showing the concentration of the highest-octane isopentane and dimethylbutane isomers in the product with a high degree of precision in contrast to the low reproducibility of the measurement of product octane.

The comparison of the relative performance of Catalysts A and B show the advantage of surface-layer platinum. Catalyst B shows an advantage of 1-2% for the highest-octane isomers with peak concentrations at lower temperatures where more favorable equilibrium is obtained. Even the surface-layer low-platinum Catalyst C shows an advantage over the high-platinum control Catalyst A, thus demonstrating that the present invention reduces requirements for costly platinum in an isomerization process. The results may be summarized as follows:

|  | Peak Research Octane Clear | Reactor Outlet Temp. at Peak, °C. |
|---|---|---|
| Catalyst A | 82.7 | 149 |
| Catalyst B | 83.0 | 132 |
| Catalyst C | 82.8 | 138 |

The temperature at peak Research Octane does not necessarily correspond to the temperature at which the aforementioned $C_5$ and $C_6$ isomers reach a peak, due to the influence of other product isomers on Research Octane. However, the conclusions with respect to catalyst performance are consistent.

We claim:

1. A process for isomerizing isomerizable hydrocarbons to form an isomerization product which process comprises contacting the isomerizable hydrocarbons with a bed of catalyst particles comprising a refractory inorganic-oxide support, from about 1 to 15 mass % of a Friedel-Crafts metal halide and from about 0.01 to 2 mass % on an elemental basis of a surface-layer platinum-group metal component, wherein the average concentration of platinum-group metal component on a 100-micron surface layer of the catalyst particles is at least 1.5 times the average magnitude of the concentration of platinum-group metal component in the central core of the catalyst particles.

2. The process of claim 1 wherein the isomerization conditions comprise a temperature of about 40° to 250° C., a pressure of about atmospheric to 100 atmospheres, a liquid hourly space velocity of about 0.5 to 5 liquid volumes per hour of isomerizable hydrocarbons per volume of catalyst, and a mole ratio of hydrogen to isomerizable hydrocarbon feed of about 0.01 to 5.

3. The process of claim 1 wherein the temperature is about 40° to 150° C.

4. The process of claim 1 wherein the mole ratio of hydrogen to hydrocarbons in the process reactor effluent is less than about 0.05.

* * * * *